United States Patent [19]

Deutsch

[11] 4,219,539

[45] Aug. 26, 1980

[54] IMMUNOCHEMICAL DIAGNOSTIC METHOD FOR GASTRIC CANCER

[76] Inventor: Emmanuel Deutsch, 469 Beacon St., Boston, Mass. 02115

[21] Appl. No.: 881,137

[22] Filed: Feb. 24, 1978

[51] Int. Cl.³ .................... G01N 33/50; G01N 33/48; G01N 27/26; G01N 21/82
[52] U.S. Cl. .................................... 424/8; 23/230 B; 424/9; 424/12; 424/104
[58] Field of Search .................. 424/8, 9, 12, 104; 23/230 B

[56] References Cited

PUBLICATIONS

Piper (ed.), Stomach Cancer, UICC Tech. Report Series, vol. 34, Geneva, 1978, pp. 85-97.
Apffel et al., Cancer Res., vol. 33, Jan. 1973, p. 112.

*Primary Examiner*—Anna P. Fagelson
*Attorney, Agent, or Firm*—Abraham A. Saffitz

[57] ABSTRACT

Using anti-IgG and anti-Fc sera which is reacted with gastric cancer juice from a patient by double diffusion on Ouchterlony agarose, there is repeatedly obtained a double precipitin line. Under immunoelectrophoresis, anodic displacement of anti-IgG and anti-Fc sera is observed. The $\beta_1$ to $\alpha_1$ precipitin line with anti-IgG and anti-Fc is thus formed to be characteristic of gastric cancer juice. These double precipitin lines correspond to an antigen-antibody complex which are uniquely identified by Ouchterlony immunodiffusion assay with these anti-immunoglobulin sera. Only a single precipitin line is formed between gastric cancer juice and anti-Fab serum.

Both with anti-IgG and anti-Fc, various lines are obtained under immunoelectrophoresis with different mobilities, from gamma to $\alpha_1$. With anti-Fab, however, there is no displacement toward the anode. Normally, Fc seldom moves beyond the site of origin. Thus, both IgG and Fc of gastric cancer juice exhibit a displacement toward the anode.

1 Claim, No Drawings

IMMUNOCHEMICAL DIAGNOSTIC METHOD FOR GASTRIC CANCER

BACKGROUND OF THE INVENTION (A) Field of the Invention

This invention is generally in the field of differentiating between malignant and benign tumors of the gastric mucosa and specifically in the field of gastric cancer diagnosis as a tool in early and reproducible detection of gastric cancer by assaying the gastric juice of the patient.

(B) Description of the Prior Art

It is generally accepted among immunologists that tumors may be regarded as invasive grafts of tissue which should evoke homograft reactions in so far as they possess antigens foreign to their hosts. Thus, tumors are subject to principles governing immunological tolerance (see Humphrey and White, *Immunology for Students of Medicine*, 3rd Edition 1970, 2nd printing 1971, Blackwell Publications, page 580).

It is also accepted that antigens have been detected in human carcinomas of the gastrointestinal tract which are absent from the corresponding normal tissue of their hosts but are present in embryonic tissues of the same species. These antigens represent the product of genes which are normally repressed in adult cells (see "Immunology . . . " as cited above, page 583). These last named antigens are presumed to represent products of genes which are normally repressed in adult cells and are distinctly different from virus induced tumors or tumors elicited by chemical carcinogens.

The invention has found and reported with his co-workers in *Cancer Research*, volume 33, January 1973, that an antigen which is different from and distinct from Gold's carcinoembryonic antigen is present in gastric cancer secretions and reacts immunochemically to give one precipitin line on double diffusion in agar gel.

DISTINCTIONS OF INVENTION OVER PRIOR ART

The unexpected improvement in immunological particularity is based upon the discovery that the $B_1$ to $a_1$ line more characteristic of gastric cancer juice corresponds to an antigen-antibody complex and, with this in mind, the assay of various gastric juices on Ouchterlony immunodiffusion with anti-immunoglobulin sera demonstrated that all the juices gave precipitin lines with both IgG and IgA but that IgG produces a double line with gastric cancer juice, but only one line with juices from normal subjects or subjects with gastric ulcer.

After testing gastric juices by the Ouchterlony method with anti-IgG an assay with anti-Fab and anti-Fc demonstrates that anti-Fab consistently produces one single line whatever the normal or pathological condition while the anti-Fc serum, like the anti-IgG, produces a double line.

Since both native IgG and Fc fragments complex with an antigen of gastric juice and do so preferentially in juices from gastric cancer patients, gastric juices are immunoelectrophoresed against anti-IgG, anti-Fc and anti-Fab. Both with anti-IgG and anti-Fc, various lines are obtained with different mobilities from gamma to $a_1$. With anti-Fab, however, there is no displacement toward the anode. Normally Fc seldom moves beyond the site of origin. Thus, both IgG and Fc of gastric cancer juice exhibit a displacement toward the anode.

The improvement in immunodiffusion procedure using the anti-IgG, anti-Fab and anti-Fc sera over the inventor's prior procedure in *Cancer Research*, volume 33, January 1973, introduces a higher degree of accuracy and a more reproducible identification of gastric cancer than in the earlier work.

OBJECTS OF THE INVENTION

An object of the invention is to provide an improved immunochemical identification system to diagnose crucial immunochemical alterations of gastric juice associated with cancer whereby gastric cancer can be detected, diagnosed or confirmed based upon histological evidence.

A further object of the invention is to provide accurate and highly reproducible diagnosis of gastric cancer from immunochemical examination of gastric juice from a patient to satisfy three critical criteria:

(1) a double precipitin line on Ouchterlony agarose immunodiffusion (double diffusion in two dimensions) against anti-IgG and anti-Fc sera;
(2) anodic displacement on immunoelectrophoresis against anti-IgG and anti-Fc sera;
(3) a sinuous characteristic to the precipitin line indicative of complex formation.

In contradistinction to these double precipitin line formations in (1) above, anti-IgA never produces a double line and anti-Fab serum does not create anodic displacement of the precipitin line.

A further object of the invention is to improve the accuracy of diagnosis of gastric cancer by testing gastric juice and relating this testing to confirmatory testing by fiberoptic gastroscopy and histological examination.

Other and further objects of the invention will become apparent from the examples of preferred testing embodiments and the more detailed explanation in the following description.

SUMMARY OF THE INVENTION

The invention provides an accurate and highly reproducible diagnosis of gastric cancer by the Ouchterlony procedure for double diffusion in two dimensions whereby the unique specificity of the precipitin reaction identifies the cancer in the gastric cancer juice against the following anti-sera, anti-IgG and anti-Fc to show:

(a) the development of a double precipitin line for each of the sera, and
(b) a sinuous or warp line.

A third critical test is:

(c) the movement toward the anode, i.e., anodic displacement, under immunoelectrophoresis of both precipitin lines due to anti-IgG and anti-Fc sera.

CONFIRMATORY FINDINGS

The early detection of gastric cancer is one of the major unsolved problems in gastroenterology. The known, clinical, endoscopic and histological criteria indicate a condition of malignancy beyond which salvage is not practical or possible. Compounding the problem is the recognition of advanced or inoperable grades of gastric neoplasm and the prevalent experience that intestinal metaplasia is not reliable as a sign or a marker of a salvageable cancer precursor state.

A multiple biopsy procedure by fiberoptic gastroscopy has been developed by the present inventor which, for the first time, presents a new image of salvageable gastric cancer if combined with the immunological gastric detection procedure of the present invention.

A new image of salvageable gastric cancer is now available by means of fiberoptic gastroscopy. A slower rate of invasiveness is a clinical feature of these patients with a higher survival rate and an improved life style even with recurrence. It is crucial to differentiate benign from malignant hemorrhagic gastritis. A single positive biopsy can do this.

The fear of provoking further hemorrhage by multiple biopsytaking has no basis. It has been the inventor's personal experience over the past four years that hemorrhage is not provoked by gastric biopsy. It is only necessary to selectively take multiple biopsies from a localized lesion before the suspect gastric site becomes covered with a mucinous exudate.

Gastroscopic monitoring of the evolution of malignant hemorrhage gastritis in association with gastric cancer reveals that the gastritis component is the primary lesion and ulcer or polypoid lesions are secondary. This form of hemorrhagic gastritis may have a variable time-course of hemorrhage and is frequently associated with partial and even complete healing of the gastric ulceration and its later recurrence. Scar and ridge formation, as well as fusion of folds, are selectively directed targets for multiple positive biopsies. Biopsies and resected tissue specimens are usually well differentiated as well as undifferentiated adenocarcinoma.

During the past three years the inventor has found ten intramucosal gastric cancers among forty-six of all grades of gastric neoplasms for an incidence of twenty per-cent. Stringent surveillance of endoscopic, pathologic and immunologic markers is paramount.

Human Ig is unique among the immunoglobulins in that the rate of catabolism, e.g., the fraction of total intravascular Ig catabolized daily, increases with the concentration of IgG in the blood. Thus, when the IgG serum levels are raised, as in certain types of cancer, e.g., myeloma, the half life in the body may be shortened from its normal value of about twenty days. Thus, the patient may suffer from antibody deficiency. The control of the catabolic rate is due to the Fc piece of the IgG heavy chain, which is identified by pepsin digestion in accordance with the formula $IgG = Fc + 2Fab$.

It is accepted that in all mammalian species, the structure of IgG antibody molecules is suited to the function of combining with antigens of all shapes and sizes. The two Fab fragments are the two arms of the antibody which are recovered by treatment with pepsin and the knob or apex between the arm is called the Fc piece. The two combining sites of IgG antibody are the ends of the two Fab arms and the apex or knob at the middle is the Fc piece from which the two arms are flexibly hinged, spacing the two combining sites of the Fab piece at a variable distance of about 230 Angstrom units.

The search for immunological features in the inventor's earlier study of gastric cancer juice uncovered a characteristic wavy or sinuous precipitin line on immunoelectrophoresis in the $B_1$ to $\alpha_1$ region but this alone did not look promising because of other lines between the cathode and the $\alpha_1$ region. No line was observed with normal gastric juice.

The Ouchterlony immunodiffusion procedure with anti-immunoglobulin sera showed normal gastric juice to give a precipitin line with IgG and IgA but with gastric cancer juice only IgG produced a double precipitin line by the Ouchterlony procedure. Remarkably, only one line with IgG was found in a patient with gastric ulcer but no malignancy.

The anti-Fab and anti-Fc assay then was tried with normal and cancerous gastric juice to find that anti-Fab produces a single precipitin line with both normal and cancerous juice while anti-Fc produces a double line.

To further pin down the distinction between the knob portion of IgG and the two arms, the Fc pieces, it is clear that with the single precipitin line formed with anti-Fab, the normal combining sites for normal gastric juice is not the characterizing site in the present cancer test. Instead, it is the knob portion, Fc, and the IgG itself, and these, surprisingly, are selected by the anti-IgG and anti-Fc sera for selective precipitin lines in the form of a double line.

The displacement of the precipitin line by immunoelectrophoresis toward the anode for both IgG and Fc of gastric cancer juice corroborates the formation of the complex between gastric IgG and antigen. The appearance of a double or multiple lines is indicative of a variable ratio of antigen/IgG or antigen/Fc.

The early attempts at characterization of the antigen in gastric secretions from cancer patients make it appear that a protein structure similar to $\alpha_1$, anti-trypsin and an $\alpha_1$ acid glycoprotein, or both, may be the structure involved. It is evident that the antigen is highly mobile, e.g., in the $\alpha$ range of mobility under immunoelectrophoresis, and has a greater mobility than IgG or Fc fragments. There is also evidence that the antigen has polyanionic characteristics.

The primary form of malignant hemorrhagic gastritis appears to be associated with the vascular tumor associated antigen, which is the antigen of the invention. Thus, this malignant form of hemorrhagic gastritis appears to be the primary lesion associated with the vascular tumor associated antigen.

PREFERRED EMBODIMENT OF THE INVENTION

The following examples illustrate a preferred embodiment of the invention for:
(1) the collection and processing of gastric cancer juice specimens;
(2) carrying out the immunodiffusion procedure; and
(3) carrying out the immunoelectrophoresis procedure for the diagnosis of gastric cancer.

EXAMPLE 1. COLLECTING AND PROCESSING

Gastric juice specimens are collected from patients through a nasagastric tube and also through the endoscope during gastroscopy. The fasting specimen is discarded, but subsequent juice is brought up to a basic pH by the introduction of 5% sodium bicarbonate intragastrically in order to inactivate pepsin.

After collection the gastric juice is dialyzed for 3 to 5 days against 0.005 M TRIS in the refrigerator with two changes of dialyzing buffer. It is then lyophilized and stored frozen until it is used. Ten milligrams of each lyophilate is solubilized in 0.5 milligrams of B-2 barbital buffer for use in testing. B-2 barbital buffer is a standard buffer whose preparation is described in Volume II, Appendix II, at page 372 of the text book "Methods in Immunology and Immunochemistry" edited by Williams and Chase, Academic Press 1968. Its use in electrophoresis is described at page 61 of the same volume. TRIS is the accepted terminology for a buffer prepared from tris (hydroxymethyl) aminomethane whose preparation is described in Volume II, Appendix II, at page 380 of "Methods in Immunology and Immunochemistry", edited by Williams and Chase, Academic Press 1968.

EXAMPLE 2. IMMUNODIFFUSION

20 λ of the sample is loaded into the wells of the pre-made Ouchterlony plates (Meloy Labs., Inc., 6715 Electronic Drive, Springfield, Virginia 22151). They are reacted for 2 days in a moist chamber at room temperature. Afterwards the unreacted protein is eluted out with normal saline. The slides are then dried, stained with 0.1% amido black in water and destained with a solution of 50% methanol, 2% acetic acid and 5% glycerine.

(a) The standard procedure of immunodiffusion in wells is described in Volume III, "Methods in Immunology and Immunochemistry", pages 147 through 159, particularly page 151.

(b) Amido black is a standard black stain whose preparation, identification and use in double diffusion in plates is described at page 153, Volume III, "Methods in Immunology and Immunochemistry", and in double diffusion at page 173. Additional descriptions are at pages 195, 215, 216, 219, 283, 285, 297, 298, 319 and 470 of this text.

(c) The anti-IgG and anti-Fc are supplied by Behring Diagnostics, American Hoechst Corporation, Somerville, New Jersey 08876. These anti-sera are prepared by the papain fragmentation method generally described by Edelman and Marchalones at pages 406 and 407 in Volume I "Methods in Immunology and Immunochemistry", edited by Williams and Chase, Academic Press 1967.

EXAMPLE 3. IMMUNOELECTROPHORESIS

10 λ of the sample is loaded into the wells of the commercial per-made agarose immunophoresis plate (Millipore Biomedia, Acton, Massachusetts 01720) in two applications. The plate is electrophoresed for 35 minutes at 100V (the buffering material barbital B-2 buffer, pH 8.6). The troughs are then doubly loaded with the anti-serum and the plate is allowed to diffuse for 2 days at room temperature in a moist chamber. Subsequently the slide is pressed dry and processed and stained in a manner similar to the immunodiffusion plates.

Immunoelectrophoresis is carried out by the standard method in agarose plates as generally described at pages 237 through 273 in Volume III of "Methods of Immunology and Immunochemistry" and the conditions at pages 251 through 257 are followed for the micro technique specifically described at pages 269 through 273. However, the micro technique described at pages 265 through 269 may be used with equally good results.

RESULTS

A study of twenty-nine patients was carried out, twelve of whom had histology confirmed gastric cancer.

The three criteria of gastric cancer juice alteration as determined by Examples 1, 2 and 3 above are:

(1) a double precipitin line on Ouchterlony immunodiffusion against anti-IgG and anti-Fc;

(2) anodic displacement of the precipitin line on immunoelectrophoresis against anti-IgG and anti-Fc; and (3) a sinuous characteristic of the precipitin line in (2) which indicates complex formation for gastric cancer juice in the immunoelectrophoresis procedure.

Of the twelve patients with gastric cancer, ten satisfied the Fc anodic displacement, making the test 80% positive diagnosis.

Of the remaining seventeen patients, all of whom had gastric ulcer, fifteen showed no reaction with anti-IgG and no reaction with anti-Fc and there was no anodic displacement of the precipitin line between gastric juice and IgG or with anti-Fc. Of these seventeen ulcer patients there were two false positives.

In the diagnostic tests carried out for the above twenty-nine patients, the important corroborative test carried out is a new system of multiple biopsies to determine a gastroscopic visual end point for proper sampling and histological examination.

The search for a gastroscopic visual end point climaxes a ten year effort by the inventor for endoscopic criteria to correlate with precursor lesions of chronic atrophic gastritis and intestinal metaplasia and with immunochemical criteria. All gastroscopies under the inventor's procedure are accompanied by at least 9 biopsies: 3 from the antrum, 3 from the body and 3 from the fundus. No correlation is found between the surface aspect and histology of biopsies. Many biopsies show focal areas of varying degrees of inflammation but no characteristic visual end point is available to indicate to the experienced endoscopist that selective endoscopic directed biopsy taking would display the presence or degree of precursor lesions nor would they improve the early detection of localized gastric cancer.

Stage I intramucosal gastric cancer is difficult to recognize from classic descriptions of the past thirty years where emphasis was always placed on the characteristics of the far advanced infiltrating lesions. The new image of early gastric cancer in the natural history of this cancer is now available by means of fiberoptic gastroscopy. One differentiating clinical feature of these patients with Stage I cancer who have a high mucosal cancer may be contained within its mucosa and submucosa for more than five years before penetrating the main muscular coat and subsequent extension to regional lymph nodes. During the past three years four out of ten mucosal cancer patients who were admitted to the hospital at which the inventor is Chief of Enterology exhibited mild gastrointestinal bleeds due to erosive hemorrhagic gastritis. Remarkably, multiple positive gastric biopsies did not aggravate the degree of hemorrhage. It thus became obvious that the best hope of detecting an early mucosal cancer is in searching for it in the freshly diagnosed gastric ulcer or polyp. The ulcer may have completely healed and still its scar tissue may provide positive biopsies before the ulcer breaks down again. Thus, the mucosal change may be ulcerative, polypoid or flat, but is not infiltrative.

Recognition of the differentiation of benign from malignant erosive gastric changes requires follow up endoscopy to evaluate crucial mucosal changes particularly in selecting sites for biopsy material. In the past three years, 10 mucosal cancers among 46 gastric cancers of all grades were identified and resected for a 21% incidence of salvageable cancer.

This finding of 21% of salvageable gastric cancers represents a slow growing lesion with a 90% survival for an excellent life style.

For selective endoscope directed biopsy, the endoscopic visual end points of early Stage I intramucosal gastric cancer comprise the following:
1. gastric ulcer or its scar
2. polyp
3. malignant erosive gastritis
4. erosive narrowing or fusion of folds.

As the lesion is assessed under direct endoscopic examination it is important to select, in advance of biopsy, those sites that may yield the most positive biopsies before the field is obscured by iatragenic hemorrhage. The endoscopic visual end points outlined above are crucial for the directed endoscopic biopsy which will then make the histological diagnosis. The 9 biopsies are taken as above.

Having thus disclosed, what I claim is:

1. A diagnostic method for distinguishing normal gastric juice from cancerous gastric juice in a human patient comprising:

collecting first a fasting gastric juice sample from a patient through a tube, discarding said fasting sample and then collecting a gastric juice sample to which alkali is added intragastrically to inactivate pepsin by raising the pH above 7;

dialyzing the subsequent sample against 0.005 molar tris buffer to remove interfering substances;

liophilizing the dialyzed material;

solubilizing the lyophilate in a small amount of barbital buffer in a ratio of about ten milligrams per ½ milligram of buffer to provide a test sample;

testing the sample against anti-IgG and anti-Fc in the wells of a Ouchterlony plate by reacting in a moist chamber until a precipitin line appears, eluting unreacted material, drying the plate, staining with amido black and destaining with solvent, further testing the sample by double loading against anti-IgG and anti-Fc in the wells of an immunoelectrophoresis plate, the same buffered with barbital at pH 8.6 and electrophoresed at 100 volts for 35 minutes and diffused for 2 days in a moist chamber, eluting unreacted material, drying said plate, staining with amido black and destaining;

a double precipitin line on the Ouchterlony plate indicating a positive cancer with anti-IgG and anti-Fc in the first immunodiffusion;

the anodic displacement of the anti-IgG and anti-Fc precipitin line on the electrophoresis plate indicating a cancer positive diagnosis; and the sinuous characteristic of the precipitin line in the immunoelectrophoresis plate indicating a complex formation associated with a cancer positive diagnosis.

* * * * *